United States Patent
Lee et al.

(10) Patent No.: US 11,607,493 B2
(45) Date of Patent: Mar. 21, 2023

(54) INITIAL TOTAL DAILY INSULIN SETTING FOR USER ONBOARDING

(71) Applicant: INSULET CORPORATION, Acton, MA (US)

(72) Inventors: Joon Bok Lee, Acton, MA (US); Mengdi Li, Westford, MA (US); Jason O'Connor, Acton, MA (US); Yibin Zheng, Hartland, WI (US)

(73) Assignee: INSULET CORPORATION, Acton, MA (US)

( * ) Notice: Subject to any disclaimer, the term of this patent is extended or adjusted under 35 U.S.C. 154(b) by 328 days.

(21) Appl. No.: 16/840,483

(22) Filed: Apr. 6, 2020

(65) Prior Publication Data

US 2021/0308377 A1   Oct. 7, 2021

(51) Int. Cl.
*G08B 1/08* (2006.01)
*A61M 5/172* (2006.01)
(Continued)

(52) U.S. Cl.
CPC .......... *A61M 5/1723* (2013.01); *G16H 10/40* (2018.01); *G16H 10/60* (2018.01); *G16H 20/17* (2018.01);
(Continued)

(58) Field of Classification Search
CPC ............ A61M 5/1723; A61M 2202/07; A61M 2205/3584; A61M 2205/50;
(Continued)

(56) References Cited

U.S. PATENT DOCUMENTS 303,013 A     8/1884  Horton
2,797,149 A   6/1957  Skeggs
(Continued)

FOREIGN PATENT DOCUMENTS

AU   2015200834 A1   3/2015
AU   2015301146 A1   3/2017
(Continued)

OTHER PUBLICATIONS

US 5,954,699 A, 09/1999, Jost et al. (withdrawn)
(Continued)

*Primary Examiner* — Toan N Pham
(74) *Attorney, Agent, or Firm* — Goodwin Procter LLP

(57) ABSTRACT

Disclosed are techniques to establish initial settings for an automatic insulin delivery device. An adjusted total daily insulin (TDI) factor usable to calculate a TDI dosage may be determined. The adjusted TDI factor may be a TDI per unit of a physical characteristic of the user (e.g., weight) times a reduction factor. The adjusted TDI factor may be compared to a maximum algorithm delivery threshold. Based on the comparison result, the application or algorithm may set a TDI dosage and output a control signal. Blood glucose measurement values may be collected from a sensor over a period of time. A level of glycated hemoglobin of the blood may be determined based on the obtained blood glucose measurement values. In response to the level of glycated hemoglobin, the set TDI dosage may be modified. A subsequent control signal including the modified TDI dosage may be output to actuate delivery of insulin.

20 Claims, 5 Drawing Sheets

(51) Int. Cl.
    *G16H 20/17* (2018.01)
    *G16H 40/67* (2018.01)
    *G16H 50/50* (2018.01)
    *G16H 10/40* (2018.01)
    *G16H 10/60* (2018.01)
    *G16H 50/30* (2018.01)
    *G16H 50/70* (2018.01)
    *G16H 50/20* (2018.01)
    *H04L 67/141* (2022.01)

(52) U.S. Cl.
    CPC ............ *G16H 40/67* (2018.01); *G16H 50/20* (2018.01); *G16H 50/30* (2018.01); *G16H 50/50* (2018.01); *G16H 50/70* (2018.01); *A61M 2202/07* (2013.01); *A61M 2205/3584* (2013.01); *A61M 2205/50* (2013.01); *A61M 2205/502* (2013.01); *A61M 2230/20* (2013.01); *A61M 2230/201* (2013.01); *H04L 67/141* (2013.01)

(58) Field of Classification Search
    CPC ........ A61M 2205/502; A61M 2230/20; A61M 2230/201; G16H 10/40; G16H 10/60; G16H 20/17; G16H 40/67; G16H 50/20; G16H 50/30; G16H 50/50; G16H 50/70; G16H 40/60; H04L 67/141
    See application file for complete search history.

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |

(56) References Cited

U.S. PATENT DOCUMENTS

| | | |
|---|---|---|
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2* | 10/2010 | Kanderian, Jr. ... A61B 5/14865 604/67 |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |

(56) References Cited

U.S. PATENT DOCUMENTS

| | | |
|---|---|---|
| 9,233,204 B2 | 1/2016 | Booth et al. |
| 9,486,571 B2 | 11/2016 | Rosinko et al. |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1* | 7/2019 | Michelich .......... A61B 5/14532 |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1* | 3/2005 | Davidson ................ A61M 5/20 514/6.9 |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodat et al. |
| 2009/0030398 A1 | 1/2009 | Yodat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |

(56) References Cited

U.S. PATENT DOCUMENTS

| | | |
|---|---|---|
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla et al. |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrosio et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1* | 10/2018 | Finan .................. A61M 5/178 |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |

(56) References Cited

U.S. PATENT DOCUMENTS

| | | | |
|---|---|---|---|
| 2020/0342974 A1 | 10/2020 | Chen et al. | |
| 2021/0050085 A1 | 2/2021 | Hayter et al. | |
| 2021/0098105 A1 | 4/2021 | Lee et al. | |
| 2022/0023536 A1* | 1/2022 | Graham | G16H 40/67 |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 1571582 A2 | 9/2005 |
| EP | 0801578 B1 | 7/2006 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 2004043250 A1 | 5/2004 |
| WO | 04092715 A1 | 10/2004 |
| WO | 2005051170 A2 | 6/2005 |
| WO | 2005082436 A1 | 9/2005 |
| WO | 05110601 A1 | 11/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056275 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

European Search Report for the European Patent Application No. 21168591.2, dated Oct. 13, 2021, 04 pages.

International Search Report and Written Opinion for the International Patent Application No. PCT/US2021/041954, dated Oct. 25, 2021, 13 pages.

International Search Report and Written Opinion for the International Patent Application No. PCT/US2021/047771, dated Dec. 22, 2021, 11 pages.

International Search Report and Written Opinion for the International Patent Application No. PCT/US2021/052855, dated Dec. 22, 2021, 11 pages.

Unger, Jeff, et al., "Glucose Control in the Hospitalized Patient," Emerg. Med 36(9):12-18 (2004).

Glucommander FAQ downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

European Patent Office, "Notification of Transmittal of the ISR and the Written Opinion of the International Searching Authority, or the Declaration," in PCT Application No. PCT/GB2015/050248, dated Jun. 23, 2015, 12 pages.

(56) References Cited

OTHER PUBLICATIONS

Farkas et al. ""Single-Versus Triple-Lumen Central Catheter-Related Sepsis: A Prospective Randomized Study in a Critically Ill Population"" The American Journal of Medicine Sep. 1992vol. 93 p. 277-282.
Davidson, Paul C., et al., A computer-directed intravenous insulin system shown to be safe, simple,and effective in 120,618 h of operation, Diabetes Care, vol. 28, No. 10, Oct. 2005, pp. 2418-2423.
International Search Report and Written Opinion for the International Patent Application No. PCT/US2021/016283, dated Jun. 2, 2021, 15 pages.
Gorke, A. "Microbial contamination of haemodialysis catheter connections." EDTNA/ERCA journal (English ed.) vol. 31,2 (2005): 79-84. doi:10.1111/j.1755-6686.2005.tb00399.x.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Templeton et al., "Multilumen Central Venous Catheters Increase Risk for Catheter-Related Bloodstream Infection: Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 dated Jul. 16, 2010 (OPTIS.247VPC).
International Search Report and Written Opinion in PCT/US2008/079641 (Optis.203VPC) dated Feb. 25, 2009.
Berger, ""Measurement of Analytes in Human Serum and Whole Blood Samples by Near-Infrared Raman Spectroscopy,"" Ph D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et. al.,"Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP—Endocrinol Metab, vol. 294, E15-E26, first published Oct. 23, 2007.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.
International Preliminary Report on Patentability for the International Patent Application No. PCT/US2019/053603, dated Apr. 8, 2021, 9 pages.
International Search Report and Written Opinion for the International Patent Application No. PCT/US2019/053603, dated Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech.vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).
International Search Report and Written Opinion for the InternationalPatent Application No. PCT/US2021/018297, dated May 18, 2021, 18 pages.
An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.
International Search Report and Written Opinion for the International Patent Application No. PCT/US2021/017441, dated May 25, 2021, 12 pages.
International Search Report and Written Opinion for the InternationalPatent Application No. PCT/US2021/017664, dated May 26, 2021, 16 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, dated May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, dated May 27, 2021, 16 pages.
International Search Report and Written Opinion for the International Patent Application No. PCT/US2020/065226, dated May 31, 2021, 18 pages.
International Search Report and Written Opinion for the International Patent Application No. PCT/US2021/017659, dated May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
Anonymous: "Fuzzy control system", Wikipedia, Jan. 10, 2020. URL: https://en.wikipedia.org/w/index.php?title=Fuzzy_control_system&oldid=935091190.
International Search Report and Written Opinion for the International Patent Application No. PCT/US2021/022694, dated Jun. 25, 2021, 13 pages.

(56) References Cited

OTHER PUBLICATIONS

International Search Report and Written Opinion for International Patent Application No. PCT/US2021/051027, dated Jan. 7, 2022, 16 pages.

International Search Report and Written Opinion for International Patent Application No. PCT/US2021/052372, dated Jan. 26, 2022, 15 pages.

International Search Report and Written Opinion for the International Patent Application No. PCT/US2021/046607, dated Jan. 31, 2022, 20 pages.

International Search Report and Written Opinion for the International Patent Application No. PCT/US2021/055745, dated Feb. 14, 2022, 13 pages.

International Search Report and Written Opinion for the International Patent Application No. PCT/US2020/052125, dated Aug. 12, 2020, 15 pages.

International Search Report and Written Opinion for the International Patent Application No. PCT/US2020/050332, dated Sep. 12, 2020, 12 pages.

International Search Report and Written Opinion for Application No. PCT/EP2019/060365, dated Aug. 13, 2019, 12 pages.

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, dated Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, dated May 16, 2017, 12 pages.

International Search Report and Written Opinion for the International Patent Application No. PCT/US2018/018901, dated Aug. 6, 2018, 12 pages.

International Search Report and Written Opinion for International Patent Application No. PCT/US2018/052467, dated Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.

"Read NFC Tags with an iPHone App on iOS 11", GoToTags, Sep. 11, 2017, web <https://gototags.com/blog/read-nfc-tags-with-an-iphone-app-on-ios-11/>. (Year:2017).

International Search Report and Written Opinion for International Patent Application No. PCT/US2016/063350, dated Mar. 27, 2017, 9 pages.

Extended Search Report dated Aug. 13, 2018, issued in European Patent Application No. 16753053.4, 9 pages.

International Search Report and Written Opinion for International Patent Application No. PCT/US16/18452, dated Apr. 29, 2015, 9 pages.

International Preliminary Report on Patentability dated Aug. 31, 2017, issued in PCT Patent Application No. PCT/US2016/018452, 7 pages.

International Search Report and Written Opinion for International Patent Application No. PCT/US2019/055862, dated Mar. 11, 2020.

International Search Report and Written Opinion for the International Patent Application No. PCT/US2022/013470, dated May 6, 2022, 14 pages.

International Search Report and Written Opinion for the International Patent Application No. PCT/US2022/013473, dated May 6, 2022, 13 pages.

International Search Report and Written Opinion for the International Patent Application No. PCT/US2022/019079, dated Jun. 2, 2022, 14 pages.

International Search Report and Written Opinion for the International Patent Application No. PCT/US2022/018453, dated Jun. 2, 2022, 13 pages.

International Search Report and Written Opinion for the International Patent Application No. PCT/US22/018700, dated Jun. 7, 2022, 13 pages.

International Search Report and Written Opinion for the International Patent Application No. PCT/US22/019080, dated Jun. 7, 2022, 14 pages.

International Search Report and Written Opinion for the International Patent Application No. PCT/US22/019664, dated Jun. 7, 2022, 14 pages.

International Search Report and Written Opinion for the International Patent Application No. PCT/US21/060618, dated Mar. 21, 2022, 15 pages.

Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/en/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/Issues/2473 [retrieved on Jun. 6, 2022].

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

(56) References Cited

OTHER PUBLICATIONS

Villareal et al. (2009) in: Distr. Comp. Art. Intell. Bioninf. Soft Comp. Amb. Ass. Living; Int. Work Conf. Art. Neural Networks (IWANN) 2009, Leet. Notes Comp. Sci vol. 5518; S. Omatu et al. (Eds.), pp. 870-877.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

International Search Report and Written Opinion for the International Patent Application No. PCT/US2022/012896, dated Apr. 22, 2022, 15 pages.

Glucon Critical Care Blood Glucose Monitor; Glucon; retrieved on Dec. 29, 2010 from http://www.glucon.com.

\* cited by examiner

100

INITIAL TOTAL DAILY INSULIN SETTING FOR USER ONBOARDING

BACKGROUND

Many people are diagnosed with Type 1 diabetes mellitus (TIDM) each year, according to the Food and Drug Administration. These patients may require insulin pumps and may desire to utilize an automatic insulin delivery (AID) system. However, the potential new users of AID systems have no pump parameters and no historical total daily insulin (TDI) data at all and nearly 50% of the new users will enter into honeymoon phase, where patients' insulin needs vary rapidly. TDI is a total amount of insulin delivered to a user in a day. It is based on how much insulin a user needs for the day. The honeymoon period may last up to six months, or as long as it takes the insulin-producing cells of the pancreas to die.

TDI of newly diagnosed patient may be determined in a number of way. Presently, initialization of TDI for a newly diagnosed diabetic patient is based on: 1) weight only; and 2) weight, glycated hemoglobin (HbA1C) (which is used for manual insulin delivery) and ketones (For example, TDI may be determined using a formula such as TDI=(−38)+ 1.4*weight (kg)+0.17*HbA1C (in mmol/mol)+4.3*ketones (mmol/L)). When weight alone is used, children with moderate hyperglycemia but without ketonuria or acidosis may be started with a single daily subcutaneous injection of 0.3-0.5 u/kg of intermediate-acting insulin alone. Children with hyperglycemia and ketonuria but without acidosis or dehydration may be started on a TDI established using a formulation of 0.5-0.7 u/kg of intermediate-acting insulin.

The TDI determined in this manner is only a generalization and may not satisfy needs of all new patients. It would be beneficial and advantageous to have a system, a device and/or a technique for optimizing a TDI for newly-diagnosed diabetic uses who may desire to use an automatic insulin delivery system.

SUMMARY

Disclosed is a non-transitory computer readable medium embodied with programming code executable by a processor, and the processor when executing the programming code is operable to perform functions, and a process. A processor may be operable to receive a request via a graphical user interface to establish initial settings for an automatic insulin delivery device. An input of at least one physical characteristic of a user may be received. An adjusted total daily insulin factor usable to calculate a total daily insulin dosage may be determined. The adjusted total daily insulin factor may be a total daily insulin per unit of the user's weight reduced by a reduction factor. A comparison result generated by comparing the adjusted total daily insulin factor to a maximum algorithm delivery threshold. A total daily insulin dosage may be set based on the comparison result. Blood glucose measurement values may be obtained over a period of time. Based on the obtained blood glucose measurement values, a level of glycated hemoglobin of a user may be determined. In response to the determined level of glycated hemoglobin, the set total daily insulin dosage may be modified to provide a modified total daily insulin dosage. A control signal may be output that includes the modified total daily insulin dosage instructing a controller of a drug delivery device to actuate delivery of insulin according to the modified total daily insulin dosage.

Also disclosed is a device that includes a processor, a memory, a wireless communication device and an artificial pancreas application executable by the processor. The processor may be operable to execute programming code and applications including the artificial pancreas application. The memory may be coupled to the processor and operable to store programming code, an artificial pancreas application and data. The wireless communication device may be operable to wirelessly communicate with a paired device and communicatively coupled to the processor. The artificial pancreas application may be executable by the processor, and the processor, when executing the artificial pancreas application, is operable to perform functions. The functions may include attaining information associated with a user. An adjusted total daily insulin factor may be established. The processor may determine whether the adjusted total daily insulin factor exceeds a maximum algorithm delivery threshold. In response to a result of the determination, a total daily insulin dosage using the attained information may be set. The processor may obtain blood glucose measurement values over a period of time. Based on the obtained blood glucose measurement values, the processor may determine a level of glycated hemoglobin of a user. In response to the determined level of glycated hemoglobin, the set total daily insulin dosage may be modified to provide a modified total daily insulin dosage. A control signal may be output that includes the modified total daily insulin dosage instructing a controller to actuate delivery of insulin according to the modified total daily insulin dosage.

DETAILED DESCRIPTION

Figure 1:
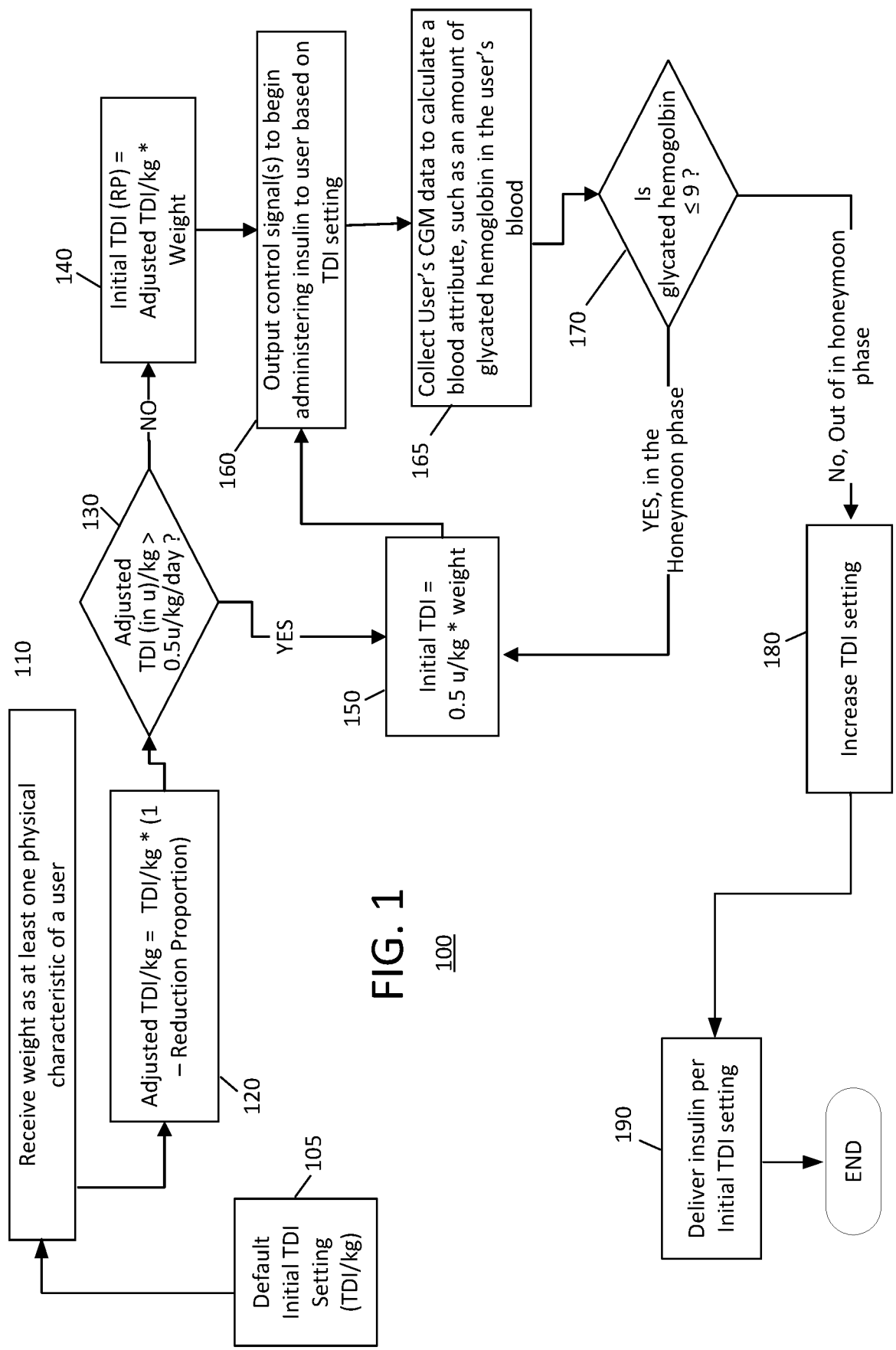
FIG. 1 illustrates an example of a process for determining an initial total daily insulin dosage related to a diabetes treatment program of a newly-diagnosed user that is onboarding.

An example provides a process that may be used with any additional algorithms or computer applications that manage blood glucose levels and insulin therapy. Such algorithms may be referred to as an "artificial pancreas" algorithm-based system, or more generally, an artificial pancreas (AP) application or automatic insulin delivery (AID) algorithm, that provides automatic delivery of an insulin based on a blood glucose sensor input, such as that received from a CGM or the like. In an example, the artificial pancreas (AP) application when executed by a processor may enable a system to monitor a user's glucose values, determine an appropriate level of insulin for the user based on the monitored glucose values (e.g., blood glucose concentrations or blood glucose measurement values) and other information, such as user-provided information, such as carbohydrate intake, exercise times, meal times or the like, and take actions to maintain a user's blood glucose value within an appropriate range. The appropriate blood glucose value range may be considered a target blood glucose value of the particular user. For example, a target blood glucose value may be acceptable if it falls within the range of 80 mg/dL to 120 mg/dL, which is a range satisfying the clinical standard of care for treatment of diabetes. Alternatively, in addition, an AP application (or AID algorithm) as described herein may be able to establish a target blood glucose value more precisely and may set the target blood glucose value at, for example, 110 mg/dL, or the like. As described in more detail with reference to the examples of FIGS. 1-5, the AP application (or AID algorithm) may utilize the monitored blood glucose measurement values and other information to determine, or the like.

The total daily insulin (TDI) described in the following description is intended as an initialization input into an automatic insulin delivery system that utilizes a closed-loop control operation and is not intended for use in open-loop control operation.

Typically, persons diagnosed with diabetes, such as Type 1, are suffering from a failure of their pancreas to produce enough insulin for their bodies to properly regulate blood glucose levels. The failure of the pancreas to produce enough insulin may be due the dying of cells of the pancreas and not being regenerated. As the cells of the pancreas die, and the amount of insulin produced by the remaining pancreas cells diminishes, a point is reached where it is recommended that the user begin receiving supplemental insulin. This time period as the pancreatic cells die off, and the user may become dependent on the supplemental insulin is referred to as the "honeymoon period." A "honeymoon period" may last, in some instances, 6-18 months given the degree of failure of the user's pancreas and the time of the user's initial diabetes diagnosis. Of course, the honeymoon period may be shorter or longer for each individual user as there is no set time period for pancreatic failure. A measurement of a user's insulin dose adjusted glycated hemoglobin (HbA1c), which may be abbreviated as IDAA1c, may be used to determine whether the user is still within the "honeymoon period," or not. In addition, the AP application or AID algorithm may determine that a user is requiring additional insulin over time as the pancreas fails.

In general, an automatic insulin delivery (AID) system can incorporate a variety of methods to 1) calculate the initial TDI based on linear relationship between TDI and weight. 2) An advantage of the described techniques and devices it that by adjusting TDI in consideration of the impact of the particular user's honeymoon phase allows the respective users to enter into closed loop systems without need for pre-existing insulin settings.

Due to the complicated and dynamic nature of the human body's response to insulin users may end up in a hypoglycemic or hyperglycemic state after being treated with insulin therapy. This outcome is undesirable for many reasons: hypoglycemia creates an immediate risk of a severe medical event (such as a seizure, a coma, or a death) while hyperglycemia creates long term negative health effects as well as the risk of ketoacidosis. Whether a person ends up in one of these states depends on a very complicated combination of many factors and sources of error.

Individuals affected with diabetes have a plethora of complicated decisions to make throughout the day to ensure a user is providing themselves with adequate insulin therapy. An automatic insulin delivery system that utilizes algorithms and/or an artificial pancreas (AP) application is operable to make many insulin delivery and insulin therapy-related decisions for a user so that the user can live their lives as close to the average non-diabetic individual as possible. In order to assist users (including new users) with making the many insulin delivery and insulin therapy-related decisions, the AP algorithm may generate alarms and notifications via a personal diabetes management (PDM) device.

In an example, an AID algorithm within any AID system may utilize the user's initial TDI to determine starting insulin delivery settings, and as time passes and additional data regarding the new user's condition is collected (for example from a continuous glucose monitor or the like), the AID algorithm may be operable to modify the starting (or initial) insulin delivery settings.

Examples of a process for initially setting insulin delivery and modifying the stating insulin delivery settings and devices for implementing a computer application are described with reference to the figures.

FIG. 1 illustrates an example of a process for initially setting insulin doses related to a diabetes treatment program. The process 100 generates a total daily insulin dosage that is usable as an input into an artificial pancreas application in a closed-loop system. In the example process 100, a personal diabetes management device executing an artificial pancreas application or automatic insulin delivery (AID) algorithm in a closed-loop system be initially launched in response to a request to begin an initial dose setting process for newly-diagnosed users. The initial dosing setting process may also be referred to as "on-boarding."

In the example process 100 of FIG. 1, the artificial pancreas (AP) application or AID algorithm may be operable to, in response to the initial launch (i.e., first time the application is opened on a user device or used by a first-time (i.e., new) user) or the request to begin the initial dose setting process, the artificial pancreas (AP) application or AID algorithm executing on a processor may, for example, set a default initial setting for determining total daily insulin (105). For example, the AID algorithm or AP application executing on a processor may calculate the user's default initial TDI using a relationship between TDI and weight, such as $$TDI = 0.53 \text{ u/kg} * \text{weight in kg},$$

where 0.53 is an insulin coefficient that may be based on historical clinical data for a population of newly-diagnosed diabetics, typical clinical guidance by endocrinologists as heuristic rules of thumb that provide reasonable initial glucose control, or the like.

The above value may be determined based on an assumption that a linear relationship exists between a user's weight and a user's TDI and that all user's on-boarding are in the honeymoon phase to minimize risk of hypoglycemia.

The artificial pancreas (AP) application or AID algorithm may be further operable to respond to the request or initial launch by causing a prompt to be generated and presented on a graphical user interface of a display of the personal diabetes management device (shown and described with reference to another figure). The artificial pancreas (AP) application or AID algorithm may be further operable to generate as part of the graphical user interface prompts requesting input of at least one physical characteristic of the user beginning the on-boarding process. In the process 100 example of FIG. 1, the at least one physical characteristic received as an input to the graphical user interface may be a weight of the user (110). Inputs in addition to a user's weight may also be received as inputs. For example, inputs, such as gender, age, height, body mass index, level of physical fitness, date of diagnosis as a diabetic, or the like may be received via the graphical user interface and may be stored in a memory (not shown in this example).

At 120, in response to the input of the at least one physical characteristic, the AP application or AID algorithm may execute logic to determine an adjusted total daily insulin factor (i.e., TDI/kg*(1−Reduction Proportion)). The process at 120 aims to optimize the TDI setting to minimize a user's risk of hypoglycemia and hyperglycemia. The adjustment is based on an expectation that the new user still has a portion of their pancreas functioning to produce insulin (i.e., the user is still in the honeymoon phase). Based on the assumption that every newly diagnosed user is in honeymoon phase, the process 100 at step reduces the TDI per kg by a certain proportion. In the example, the adjusted TDI factor may be equal to:

Adjusted TDI factor=0.53 u/kg*(1−X), where X is a TDI reduction proportion.

In an example, the reduction proportion may be based on a result of an evaluation performed in response to a request sent to a server. The reduction proportion may be determined using various methods. In a specific example, one or more cost functions may be defined to determine the reduction proportion of TDI per kg. The respective cost functions may be based on a high blood glucose index (HBGI) and a low blood glucose index (LBGI) that are selected to balance both hypoglycemic and hyperglycemic risk based on the expected overdose or underdose when utilizing the adjusted TDI factor versus actual clinical data (which may be used in an open-loop calculation or when a user is no longer considered "newly-diagnosed" (e.g., 6-18 months). The respective cost functions may be:
1) BGI_3h=Cost (accumulated insulin dose)=mean (HBGI or LBGI [3 hours out of 24 hours])
2) BGI_basal=Cost (basal insulin)=mean (HBGI or LBGI)
3) BGI_peak=Cost (insulin peak time)=mean (HBGI or LBGI [1.5 hours out of 24 hours])

Where HBGI and LBGI may be calculated, for example, by the following logic:

```
LBGI = 0;
HBG1 = 0;
Glucose_new = 1.509 * ((log(Glucose_current))^1.084 − 5.381);
If Glucose_current < 112.5 mg/dL:
    LBGI = 10 * Glucose_new^2
Else:
    HBGI = 10 * Glucose_new^2
```

Either HBGI or LBGI may remain at 0 depending on the value of the current glucose for which the risk is assessed. The non-zero value is utilized to calculate the cost. In other examples, values of HBGI or LBGI may be chosen or calculated based on selected relative risks of hyperglycemia and hypoglycemia.

Figure 4:
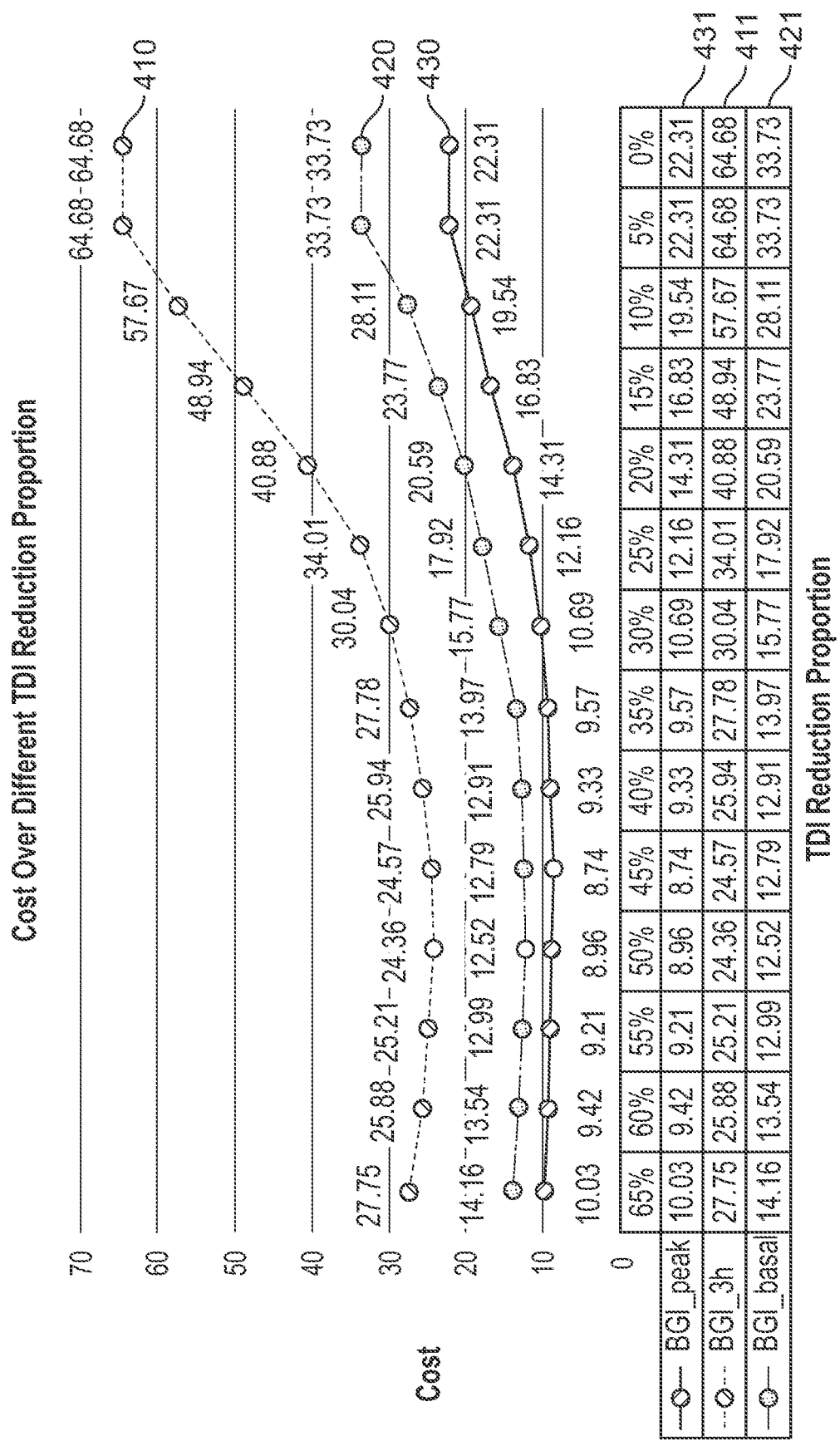
FIG. 4 illustrates a graphic including results of example functions usable in the determination of an initial total daily insulin with respect to the example process of FIG. 1.

FIG. 4 shows an example of results of the three cost functions suitable for use with the example processes of FIG. 1. FIG. 4 illustrates examples of 3 different cost functions. The top (or upper) cost function curve (labeled 410) is the BGI_3h cost function that may represent the cost of accumulated insulin doses and be based on an HGBI or LGBI over 3 hours out of 24 hours. From the curve 410 and table (bottom) row 411, the BGI_3h cost function example has a minimum cost at approximately 24.36, which corresponds to an approximate 50% TDI reduction portion. The center cost function curve (labeled 420) is the BGI_basal cost function that may represent the cost of basal insulin doses and be based on a mean value of HGBI or LGBI. From the curve 420 and table (middle row) 421, the BGI_basal cost function has a minimum cost at approximately 12.52, which corresponds to an approximate 50% TDI reduction portion. Meanwhile, the bottom (or lowest) cost function curve (labeled 430) is the BGI_peak cost function that may represent the cost of the occurrence of insulin peak time and be based on a mean value of HGBI or LGBI at approximately 1.5 hours after insulin delivery within a 24 hour period. From the curve 430 and table (top) row 431, the BGI_peak cost function has a minimum cost at approximately 8.74, which also corresponds to an approximate 45% TDI reduction portion. The table below the respective cost function curves includes a BGI_Peak row labeled 431, a BGI_3h row labeled 411, and a BGI_basal row labeled 421. Based on the output of the three cost functions, the TDI reduction proportion X may be selected to be approximately 50%. The approximately 50% value may be based on a mean value between the three cost functions (48.333%, which may round up to 50%), a majority vote where 2 out of the 3 curves indicated a 50% TDI reduction proportion, or some other selection scheme or calculation (e.g., other than averaging and rounding) may be used. In some examples, the adjusted total daily insulin factor includes an insulin coefficient, such as 0.53, 0.50 or the like. While the foregoing cost functions were explained in detail, other cost functions may be used.

Alternatively, the cost functions may be based on a weighted mean squared error (MSE) of overdose and underdose compared to the true TDI, which also balances both hypoglycemia risk and hyperglycemia risk when utilizing the adjusted TDI factor versus actual clinical data. The respective cost functions may be formulated as:

$$\text{Cost} = \frac{1}{n+m} \left( \sum_{i=1}^{n} w_1 * (TDI_{overdose} - TDI_{true})^2 + \sum_{j=1}^{m} w_2 * (TDI_{underdose} - TDI_{true})^2 \right),$$

where n is the number of overdosed cases and m is the number of underdosed TDI cases, and $w_1$ and $w_2$ are the weights to balance the hypoglycemia risk and hyperglycemia risk, respectively.

Returning to the example of FIG. 1, the process 100 at 120 may determine an adjusted total daily insulin factor usable to calculate a user's total daily insulin dosage. The adjusted total daily insulin factor may be illustrated in the formula: Adjusted TDI/kg=A*TDI/kg*(1−Reduction Proportion), where A is an insulin coefficient. The reduction proportion of an adjusted total daily insulin factor may be identified from evaluating cost functions as described above, using clinical data gathered by health organizations, or other sources of insulin history. In the example, the AP application or the AID algorithm may send a message to a server (shown in another example), requesting downloading of the one or more cost functions to a personal diabetes management device. In an alternative example, the AP application or the AID algorithm may send a request to a server, wherein the request includes either an age of a user, a weight of the user, or both for input into one or more cost functions. The server may be operable to input the either the age of the user, the weight of the user, or both into one or more cost functions. The results of the cost function may determine a minimum value that is used to determine a reduction proportion. The AP application or AID algorithm may receive the reduction proportion. The reduction proportion may be applied to the adjusted total daily insulin factor and as a result, the reduction proportion causes a reduction in the set total daily insulin dosage.

The AP application or AID algorithm may have initially set an upper bound for a maximum algorithm delivery threshold. In the example process 100, the maximum algorithm delivery threshold may be set, for example, 0.5 u/kg/day (where u is units of insulin, kg is kilograms, day is a unit of time). In an example, the maximum algorithm delivery threshold may be approximately the maximum amount of insulin that either the AP application or AID algorithm may instruct a drug delivery device to deliver to the newly-diagnosed user. For example, the maximum algorithm delivery threshold may be referred to as the approximate maximum because in some instances, the maximum amount of insulin may be relaxed (e.g., increased) or constrained (e.g., decreased) by the AP application or AID algorithm based on detected conditions of the user and historical data.

At 130, the adjusted total daily insulin factor calculated at 120 may be compared to the maximum algorithm delivery threshold. For example, the inequality may be used to determine a result for the TDI setting:

Adjusted TDI factor>maximum algorithm daily threshold (e.g., 0.5 u/kg/day).

Should the result, at 130, of the inequality be NO, the adjusted TDI factor (with the reduction proportion) is not greater than the maximum algorithm daily threshold, the process 100 may proceed to 140. For example, the AP application or AID algorithm may determine that the comparison result indicates that the adjusted total daily insulin factor is less than the maximum algorithm delivery threshold, which causes the process 100 to proceed to 140. At 140, the AP application or the AID algorithm executed by the processor may set the TDI for delivery of insulin to the user using the adjusted TDI factor (with the reduction proportion). For example, the AP application or the AID algorithm may calculate the set total daily insulin dosage using the adjusted total daily insulin factor and the weight of the user.

Conversely, at 130, if the result of the inequality is YES, the adjusted TDI factor (with the reduction proportion) is greater than the maximum algorithm daily threshold, the process 100 may proceed to 150. For example, at 130, the AP application or AID algorithm may determine that the comparison result indicates that the adjusted total daily insulin factor exceeds the maximum algorithm delivery threshold, which causes the process 100 to proceed to 150. At 150, the AP application or the AID algorithm executed by the processor may set the TDI for delivery of insulin to the user using the maximum algorithm daily threshold. In response, the AP application or AID algorithm at 150 may replace the adjusted total daily insulin factor with a predetermined total daily insulin factor, which may be, for example, 0.3-0.5 units/kilogram/day or the like. The AP application or the AID algorithm may calculate the set total daily insulin dosage using the predetermined total daily insulin factor and the weight of the user. For example, the AP application or the AID algorithm may set the TDI using the predetermined total daily insulin factor, which may be, example, 0.5 units/kilograms/day, in which case if the user weights 100 kg, the TDI is set to 50 units of insulin per day. 100 kg×0. units/kilograms/day. The actual TDI delivered may be dependent upon the inputted weight of the user. After setting the TDI either at 140 or 150, the process 100 proceeds to step 160. The device on which the AP application or AID algorithm is executing may be operable to establish communication links with other devices, such as a continuous glucose monitor (CGM) and a medical device, such as drug delivery device (shown in another example). For example, the processor of the device on which the AP application or AID algorithm is executing may be operable to generate a pairing request directed to a controller of a drug delivery device, a controller of a sensor or both. Based on a response to the pairing request from the processor, the processor of the device may establish a communication link with the controller or respective controllers. The control signal as well as other signals may be sent via the established communication link.

At step 160, the AP application or AID algorithm may output a control signal or control signals that control a drug delivery device (shown in another example) to begin administering insulin to the user based on the TDI setting from either 140 or 150. After beginning the outputting of the control signal(s) at step 160, the process 100 may proceed to 165. At 165, the AP application or the AID algorithm executed by the processor may begin collecting user blood glucose measurement values output by a continuous blood glucose monitor, also referred to as a continuous glucose monitor (CGM) (shown in another example). After a period of time of collecting the blood glucose measurement values of the user, the AP application or the AID algorithm executed by the processor may use the obtained blood glucose measurement values to calculate an attribute of the user's blood. For example, the AP application or AID algorithm may calculate, as a blood attribute, an Insulin-dose adjusted A1c (IDAA1c), or glycated hemoglobin value, for the user. In an example, IDAA1c is a model of insulin-dose adjusted glycated hemoglobin A1c, calculated as "A1c (%)+4× insulin dose (units per kilogram per 24 h (u/kg/24 hours))." Alternatively, IDAA1c is defined as actual HbA1c+(4×insulin dose (u/kg/24 h)). If IDAA1c<9, the patient is in honeymoon phase and the patient partly depends on external insulin; otherwise IDAA1c>9, the patient is no longer able to produce insulin by themselves, they fully depend on external insulin.

The AP application or the AID algorithm may evaluate the calculated glycated hemoglobin (or IDAA1c) value at 170 with reference to a standard value indicative of a honeymoon threshold value of when the pancreas fails to produce sufficient insulin. In an example, the standard value for the blood attribute, such as IDAA1c, may be a honeymoon threshold value may be approximately 9. The honeymoon threshold value of approximately 9 may represent a percentage of the user's hemoglobin that is glycated hemoglobin. If a user's calculated amount of glycated hemoglobin is equal to or less than 9, the user may still be in the honeymoon period, also known as remission phase, while user's whose calculated glycated hemoglobin is greater than 9 may no longer be in the honeymoon period.

At 170, if the calculated glycated hemoglobin is determined by the AP application or the AID algorithm to be less than 9 (i.e., YES), which indicates the user is still in the honeymoon period, the process 100 may proceed back to 150. At 150, the AP application or the AID algorithm may set the TDI to the maximum daily insulin threshold and steps 160, 165 and 170 are repeated until the determination at 170 is NO, the user's glycated hemoglobin is no longer less than or equal to 9. In the response to the NO determining, the process 100 proceeds to 180. At 180, the AP application or the AID algorithm may increase the TDI setting because a honeymoon phase upper bound is unnecessary. The TDI setting may be the default setting, which may be above the maximum daily threshold value of 0.5 u/kg*weight, such as, for example, 0.53 u/kg. After increasing the TDI setting at 180, the AP application or the AID algorithm may generate and output control signals to the drug delivery device to actuate delivery of insulin according to the increased TDI setting (190).

In the example of FIG. 1 and as described above, the calculation of initial TDI for newly diagnosed users at steps 130, 140 and 150 may be encapsulated by the following formulation:

If 0.53u/kg * (1 − X) > 0.5u/kg:
   $TDI_{initial}$ = 0.5u/kg * weight (at block 150 of FIG. 1)
Else: $TDI_{initial}$ = 0.53u/kg * (1 − X) * weight (at block 140 of FIG. 1).

In the example of FIG. 1, X can be defined as 50%, which may be determined based on a minimum value obtained from one or more cost functions as discussed above with reference to FIG. 4. If X is defined as 50% in the example, then the IF condition becomes redundant, and $TDI_{initial}$ may always be calculated by the ELSE condition.

Figure 2:
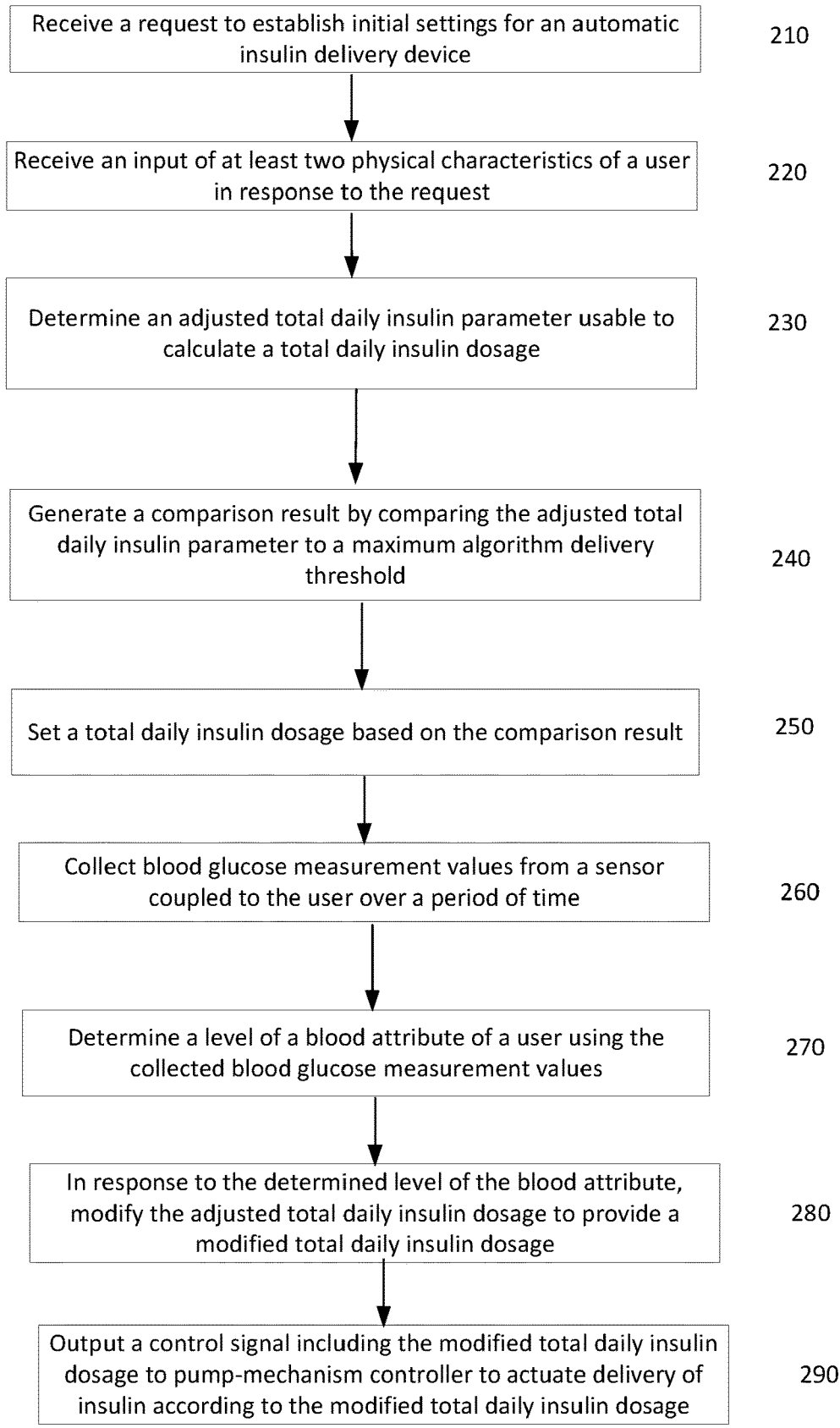
FIG. 2 illustrates another example of a process for determining an initial total daily insulin dosage related to a diabetes treatment program of a newly-diagnosed user that is onboarding.

In an alternate example, the initial TDI may be determined based on the user's weight and age. For example, when a starting TDI value is not available, the AID system can refer to the algorithm's predicted settings based on user's input weight and age to continue making insulin dosing decisions. This is predicated on the assumption that every newly-diagnosed user is in honeymoon phase, and the processes are intended to determine an optimal TDI reduction proportion to minimize the risk of both hyperglycemia and hypoglycemia for the newly-diagnosed user. FIG. 2 illustrates a flowchart of an alternative process. In the process 200, an AP application or an AID algorithm may receive a request to establish initial settings for an automatic insulin delivery device (210). In response to the received request, the AP application or AID algorithm may be operable to generate a graphical user interface and present the graphical user interface on a display device of a personal diabetes management device. The AP application or AID algorithm may receive an input of at least two physical characteristics of a user in response to the request. For example, the AP application or the AID algorithm may obtain a weight and an age of the user via the input (220). The use of a user's age may provide additional opportunities to optimize the user's total daily insulin dosage as teenagers may process insulin differently than an adult who is of the same weight because of the presence of more hormones in the teenagers.

In response to the received inputs, the AP application or AID algorithm may determine an adjusted total daily insulin factor that may be usable to calculate a total daily insulin dosage (230). For example, based on the inputted weight and age, the AP application or AID algorithm may access a lookup table of different ages and a value for a corresponding TDI per kilogram (kg).

The lookup table, for example, may be something like the table below that has a list of ages (2 years old to 24+years old) and a corresponding total daily insulin factor for each respective age. The table below as an example is available online at Researchgate.net as a publication entitled "Daily insulin requirement of children and adolescents . . . mode of therapy. Of course, other tables of data may be used or generated based on data from multiple user's, diabetes treatment organizations and research, or the like. In the table below, the total daily insulin factor may range from 0.61 (for individuals 4 years of age) to 0.80 (for individuals 14 and 15 years of age). It should be noted that the corresponding total daily insulin factors follow a bell shaped curve with a lowest value at age 2 (i.e., 0.62) to the highest factor values being at ages 14 and 15 (i.e., 0.80) to a factor value of 0.66 for those 24 years old and over.

| Age | TDI/kg |
|---|---|
| 2 | 0.62 |
| 3 | 0.64 |
| 4 | 0.61 |
| 5 | 0.66 |
| 6 | 0.66 |
| 7 | 0.68 |
| 8 | 0.68 |
| 9 | 0.73 |
| 10 | 0.72 |
| 11 | 0.73 |
| 12 | 0.77 |
| 13 | 0.79 |
| 14 | 0.80 |
| 15 | 0.80 |
| 16 | 0.78 |
| 17 | 0.76 |
| 18 | 0.73 |
| 19 | 0.74 |
| 20 | 0.69 |
| 21 | 0.66 |
| 22 | 0.69 |
| 23 | 0.69 |
| 24 | 0.66 |
| 24+ | 0.66 |

Upon determining the appropriate total daily insulin factor from the lookup table, the processor may generate an adjusted total daily insulin factor according to the following formula:

Adj. TDI Parameter=TDI/kg*weight in kg, where (TDI/kg) is the total daily insulin factor, and XX is the reduction proportion.

The process may continue at 240, at which the AP application or AID algorithm may compare the determined adjusted total daily insulin factor to an upper bound for a maximum algorithm delivery threshold, which may be a value such as 0.5 u/kg (/day)(note here TDI or 0.5 is considered a per-day value, so the total daily insulin factor may be in units of u/kg or u/kg/day). The AP application or AID algorithm may generate a comparison result based on the comparison. In response to generating a comparison result by comparing the adjusted total daily insulin factor to a maximum algorithm delivery threshold, the AP application or AID algorithm may set a total daily insulin dosage based on the comparison result at 250. In a further example, in response to setting a total daily insulin dosage, the AP application or AID algorithm may output a control signal instructing a pump-mechanism controller to actuate a pump-mechanism to administer insulin according to the set total daily insulin dosage to begin delivering insulin to the user.

In another example, the personal diabetes management device, or the like, on which the AP application or AID algorithm is executing may be operable to establish communication links with other devices, such as a continuous glucose monitor (CGM) and a medical device, such as drug delivery device (shown in another example). For example, the processor of the device on which the AP application or AID algorithm is executing may be operable to generate a pairing request directed to a controller of a drug delivery device, a controller of a sensor, or both. Based on a response to the pairing request from the processor, the processor of the device may establish a communication link with the controller or respective controllers of a sensor and/or the drug delivery device. The control signal as well as other signals may be sent via the established communication link. Upon setting the total daily insulin dosage based on the comparison result, the AP application or AID algorithm may begin outputting a control signal or signals to a medical device or drug delivery device that instructs a controller of the respective device to actuate a pump to deliver insulin according to the present total daily insulin dosage setting.

In the example process 200, the AP application or AID algorithm may be operable to receive inputs, such as blood glucose measurement values from a continuous glucose monitor. For example, the processor of the personal diabetes management device may be communicatively coupled to the continuous glucose monitor. The AP application or AID algorithm may be operable to collect the user's blood glucose measurement values (260).

At 270, the AP application or AID algorithm may be operable to determine a level of an attribute of a user' blood based on the user's blood glucose measurement values. For example, the attribute of a user' blood may be an amount of glycated hemoglobin in the user's blood. Glycated hemoglobin also referred to insulin-dose adjusted glycated hemoglobin A1c (IDAA1c) as discussed with reference to the example of FIG. 1. At 270, the AP application or AID algorithm may determine whether the level of the attribute of the user's blood exceeds a threshold value or not. For example, the AP application or the AID algorithm may be operable to verify whether the user is in honeymoon phase or not. In response to the determined level of the blood attribute, the adjusted total daily insulin dosage may be modified to provide a modified total daily insulin dosage (280). The AP application or AID algorithm may be operable to generate a control signal including the modified total daily insulin dosage and output the control signal (290). In response to the outputted control signal, the processor may be operable to output the control signal in a wireless transmission to a pump-mechanism controller of a drug delivery device (described with reference to another example). The pump-mechanism controller may be operable to actuate delivery of insulin according to the modified total daily insulin dosage.

In the example of FIG. 2 and as described above, the setting of the initial TDI for newly diagnosed user based on the comparison result at step 250 may be encapsulated by the following formulation:

If TDI/kg * (1 − Y) > 0.5u/kg:
    $TDI_{initial}$ = 0.5u/kg * weight
Else:
    $TDI_{initial}$ = TDI/kg * (1 − Y) * weight In the proposed example, the reduction proportion Y can be defined as 60% based on a minimum value obtained from one or more cost functions in a similar fashion as the selection of the 50% reduction proportion as discussed above with reference to FIG. 4. The reduction proportion may be determined using various methods. In a specific example, one or more cost functions may be defined to determine the reduction proportion of TDI per kg. The respective cost functions may be based on a high blood glucose index (HBGI) and a low blood glucose index (LBGI) that are selected to balance both hypoglycemic and hyperglycemic risk based on the expected overdose or underdose when utilizing the adjusted TDI factor versus actual clinical data (which may be used in an open-loop calculation or when a user is no longer considered "newly-diagnosed" (e.g., 6-18 months). In an example, the respective cost functions may be:

1) BGI_3h=Cost (accumulated insulin dose)=mean (HBGI or LBGI [3 hours out of 24 hours])
2) BGI_basal=Cost (basal insulin)=mean (HBGI or LBGI)
3) BGI_peak=Cost (insulin peak time)=mean (HBGI or LBGI [1.5 hours out of 24 hours])

Where HBGI and LBGI may be calculated, for example, by the following logic:

LBGI = 0;
HBGI = 0;
$CGM_{new}$ = 1.509 * ((log($CGM_{current}$))^1.084 − 5.381);
If $CGM_{current}$ < 112.5 mg/dL:
    LBGI = 10 * $CGM_{new}$^2
Else:
    HBGI = 10 * $CGM_{new}$^2

Either HBGI or LBGI, in this example, remains at 0 depending on the value of the current glucose for which the risk is assessed. The non-zero value of either HBGI or LGBI may be utilized to calculate the cost.

Figure 5:
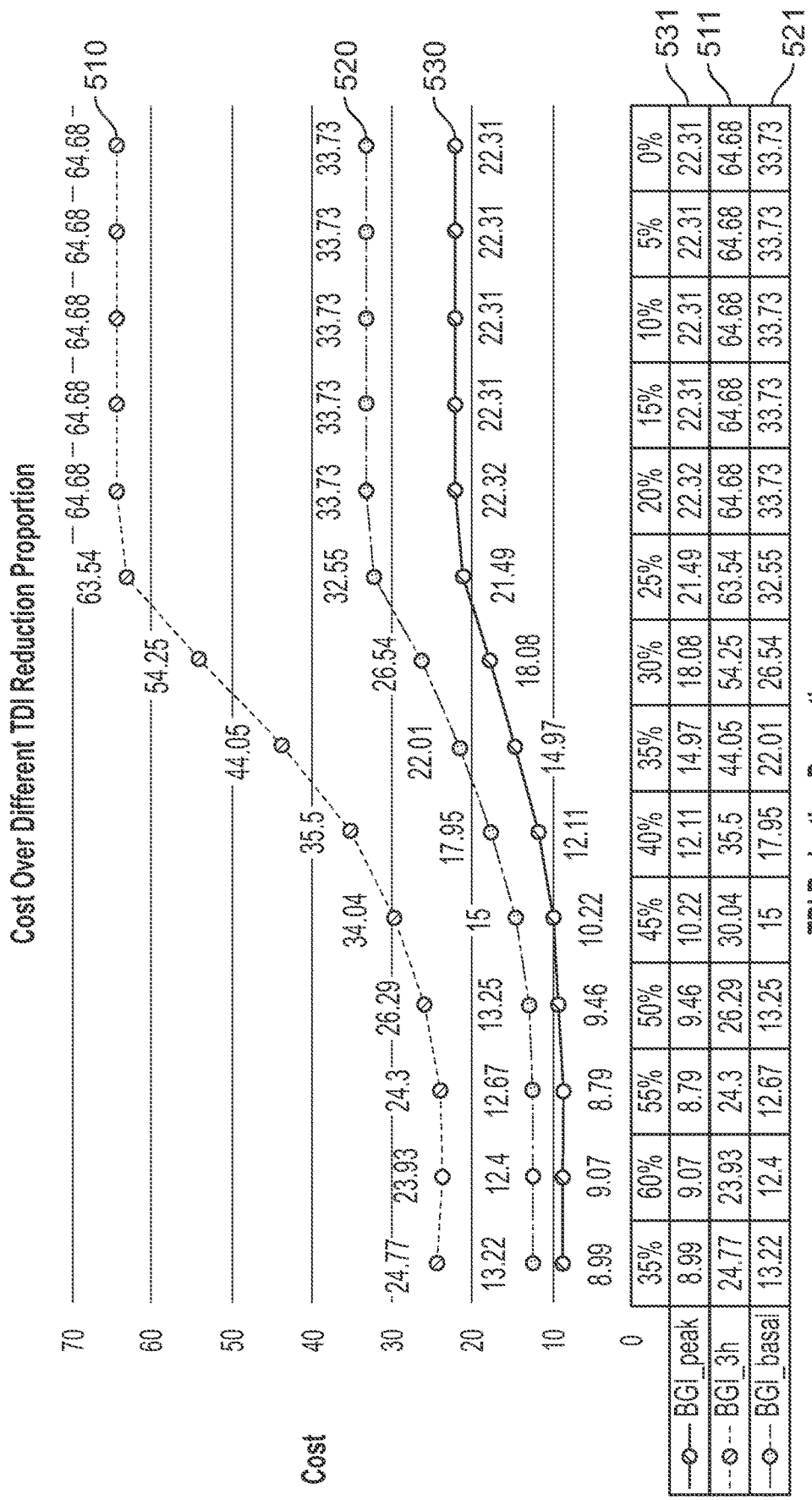
FIG. 5 illustrates a graphic including results of example functions usable in the determination of an initial total daily insulin with respect to the example process of FIG. 2.

FIG. 5 shows an example of results of the three cost functions suitable for use with the example processes of FIG. 2. FIG. 5 illustrates examples of 3 different cost functions. The top (or uppermost) cost function curve (labeled 510) is the BGI_3h cost function that may represent the cost of accumulated insulin doses and be based on an HGBI or LGBI over 3 hours out of 24 hours. From the curve 510 and table (middle) row 511, the BGI_3h cost function example has a minimum cost at approximately 23.93, which corresponds to an approximately 60% TDI reduction portion. The center cost function curve (labeled 520) is the BGI_basal cost function that may represent the cost of basal insulin doses and be based on a mean value of HGBI or LGBI. From the curve 520 and table (bottom) row 521, the BGI_basal cost function has a minimum cost at approximately 12.4, which corresponds to an approximately 60% TDI reduction portion. Meanwhile, the bottom (or lowest) cost function curve 530 is the BGI_peak cost function that may represent the cost of the occurrence of insulin peak time and be based on a mean value of HGBI or LGBI at approximately 1.5 hours after insulin delivery within a 24 hour period. From the curve 530 and table (top) row 531, the BGI_peak cost function has a minimum cost at approximately 8.79, which also corresponds to an approximate 55% TDI reduction portion. The table below the respective cost function curves includes a BGI_Peak row labeled 531, a BGI_3h row labeled 511, and a BGI_basal row labeled 521. Based on the output of the three cost functions, the TDI reduction proportion X may be selected to be approximately 60%. The approximately 60% value may be based on a mean value between the three cost functions (58.333%, which may round to 60%), a majority vote where 2 out of the 3 curves indicated a 60% TDI reduction proportion, or some other selection scheme or calculation (e.g., other than averaging and rounding) may be used. While the foregoing cost functions were explained in detail, other cost functions may be used as mentioned above with reference to FIGS. 1 and 4.

The described examples of FIGS. 1-5 provide an improved determination of TDI to optimize a newly-diagnosed user's diabetes treatment plan in a closed-loop system to further mitigate the chances of a hypoglycemic or hyperglycemic event.

In either process 100 of FIG. 1 or process 200 of FIG. 2, the AP application or AID algorithm may perform additional functions in response to the initial set up or onboarding request. For example, the AP application or AID algorithm may be operable to, in response to receipt of the request to establish initial settings for an automatic insulin delivery device, determine an availability of insulin history for the user.

In further alternate examples, different conditions may be used to determine the honeymoon period that may not be doctor-guided or based on a determination of an IDAA1c value (as in the foregoing examples) These different conditions may, for example, be used to build a classifier that predicts a honeymoon phase with gender, diabetic ketoacidosis (DKA) and other relative parameters, like a latest A1c value, as well as weight, age or both.

In further examples, the initial TDI estimates calculated according to the foregoing examples may be ignored after sufficient insulin delivery history is available, such as 48-72 hours of history based on a system that utilizes an AP application or an AID algorithm, and the insulin delivery history is the only component that is utilized for subsequent TDI calculations. For example, early in the processes 100 of FIGS. 1 and 200 of FIG. 2, the AP application or AID algorithm may perform additional functions. In an example, the AP application or AID algorithm may in response to receipt of the request to establish initial settings for an automatic insulin delivery device, determine an availability of an insulin history for the user. An insulin delivery history may include doses of insulin delivered, past TDI settings, blood glucose measurement values and the like. For example, the AP application or AID algorithm may communicate with a doctor or an automated system, such as server, that maintains diabetes-related records for the user (or the AP application or AID algorithm) to obtain a user's insulin delivery history. Alternatively, or in addition, the AP application or AID algorithm may query the user for information about a user's insulin delivery history. In response to the determination that the insulin delivery history for the user is unavailable, the AP application or AID algorithm may generate a prompt for the user to establish an initial setting for a total daily insulin dosage by inputting a weight of the user.

However, newly-diagnosed users, when determining insulin dosages on their own, may not deliver the correct amount of insulin needed to control their blood glucose. Therefore, the described examples calculate a starting TDI estimate that may be used as a component of the TDI estimate in the subsequent TDI calculations in addition to the TDI calculated from the insulin delivery history.

In the examples of FIGS. 1 and 2, the example processes may be implemented by programming code, such as an AP application or automatic insulin deliver (AID) application, that is executed by a processor. The AP application or the AID application when executed by a processor may utilize inputs and calculations as described with respect to the foregoing examples.

Figure 3:
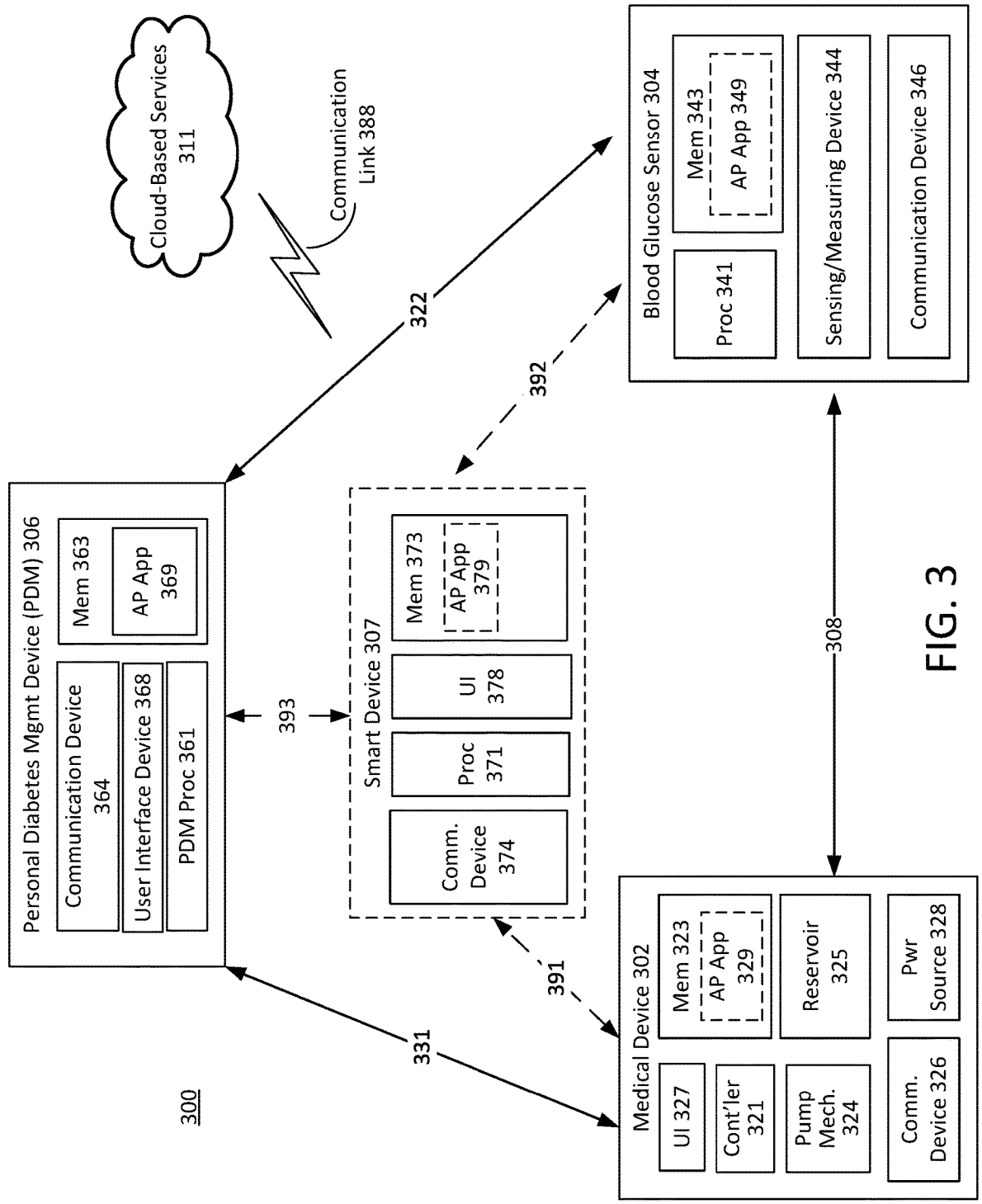
FIG. 3 illustrates a functional block diagram of drug delivery system suitable for implementing the example processes and techniques described herein including those described with reference to FIGS. 1 and 2.

It may be helpful to discuss an example of a drug delivery system that may implement the process example of FIGS. 1 and 2. FIG. 3 illustrates an example of a drug delivery system suitable for implementing the example processes and techniques described herein including those described with reference to FIGS. 1 and 2. Details of an example of a personal diabetes management device operable to establish initial settings for an automatic insulin delivery device, which may be a wearable drug delivery device, a "pod," such as an OmniPod® provided by Insulet Corp, or the like, are described with reference to the example system of FIG. 3.

The drug delivery system 300 may be operable to implement the process examples illustrated in FIGS. 1 and 2 by executing an AP application or an AID algorithm. In an operational example, the drug delivery system 300 may be operable to attain information associated with a user. The AP application or an AID algorithm may be operable to set an adjusted total daily insulin factor and determine whether the adjusted total daily insulin factor exceeds a maximum algorithm delivery threshold. In response to a result of the determination, set a total daily insulin dosage using the attained information; the AP application or AID algorithm may obtain blood glucose measurement values over a period of time. Based on the obtained blood glucose measurement values, a level of glycated hemoglobin of a user may be determined. The set total daily insulin dosage may be modified to provide a modified total daily insulin dosage in response to the determined level of glycated hemoglobin. The AP application or the AID algorithm may be operable to output a control signal including the modified total daily insulin dosage instructing a controller to actuate delivery of insulin according to the modified total daily insulin dosage.

The drug delivery system 300 may be an automatic drug delivery system that may include a medical device 302 (also referred to as "a drug delivery device" or "a wearable drug delivery device"), a blood glucose sensor 304 (also referred to as "a continuous glucose monitor" or "a blood glucose measurement device"), and a personal diabetes management (PDM) device 306. The system 300, in an example, may also include a smart device 307, which may be operable to communicate with the PDM 306 and other components of system 300 either via a wired or wireless communication link, such as 391, 392 or 393. In a specific example, the smart device 307 is coupled to the PDM 306 only via a wireless communication link 393, which may be a wireless communication link that utilizes the Bluetooth communication protocol or the like.

In an example, the medical device 302 may be attached to the body of a user, such as a patient or diabetic via, for example, an adhesive, and may deliver any therapeutic agent, including any drug or medicine, such as insulin, morphine or the like, to the user. The medical device 302 may, for example, be a wearable device worn by the user. For example, the medical device 302 may be directly coupled to a user (e.g., directly attached to a body part and/or skin of the user via an adhesive or the like). In an example, a surface of the medical device 302 may include an adhesive (not shown) to facilitate attachment to a user.

The medical device 302 may include a number of components to facilitate automatic delivery of a drug (also referred to as a therapeutic agent) to the user. The medical device 302 may be operable to store the drug (i.e., insulin) and to provide the drug to the user. The medical device 302 is often referred to as a pump, or an insulin pump, in reference to the operation of expelling insulin from the reservoir 325 for delivery to the user. While the examples refer to the reservoir 325 storing insulin, the reservoir 325 may be operable to store other drugs or therapeutic agents, such as morphine or the like, that are suitable for automatic delivery.

In various examples, the medical device 302 may be an automatic, wearable drug delivery device. For example, the medical device 302 may include a reservoir 325 for storing the drug (such as insulin), a needle or cannula (not shown) for delivering the drug into the body of the user (which may be done subcutaneously, intraperitoneally, or intravenously), and a pump mechanism (mech.) 324, or other drive mechanism, for transferring the drug from the reservoir 325, through a needle or cannula (not shown), and into the user. The pump mechanism 324 may be fluidly coupled to reservoir 325, and communicatively coupled to the medical device controller 321. The medical device 302 may also include a power source 328, such as a battery, a piezoelectric device, or the like, for supplying electrical power to the pump mechanism 324 and/or other components (such as the controller 321, memory 323, and the communication device 326) of the medical device 302. Although not shown, an electrical power supply for supplying electrical power may similarly be included in each of the sensor 304, the smart device 307 and the PDM device 306.

The blood glucose sensor 304 may be a device communicatively coupled to the PDM processor 361 or controller 321 and may be operable to measure a blood glucose value at a predetermined time interval, such as every 5 minutes, or the like. The blood glucose sensor 304 may provide a number of blood glucose measurement values to the AP applications (e.g., 329, 349, 369, or 379) operating on the respective devices (e.g., 302, 304, 306, or 307). While the AP applications 329, 349, 369 and 379 were discussed in detail and shown in the system 300 example of FIG. 3, the AP applications 329, 349, 369 and 379 may be replaced with an AID algorithm that is also operable to control and communicate with connected devices, such as medical device 302 and sensor 304, and manage a personal diabetes treatment program, and provide the functions and services as described herein.

The medical device 302 may provide the insulin stored in reservoir 325 to the user based on information (e.g., blood glucose measurement values, predicted future blood glucose measurements, evaluations based on a user request for a bolus, an user interaction with PDM 306, medical device 302, sensor 304 or smart device 307), evaluations of missing blood glucose measurements and the other information provided by the sensor 304, smart device 307, and/or the management device (PDM) 306. For example, the medical device 302 may contain analog and/or digital circuitry that may be implemented as a controller 321 for controlling the delivery of the drug or therapeutic agent. The circuitry used to implement the controller 321 may include discrete, specialized logic and/or components, an application-specific integrated circuit, a microcontroller or processor that executes software instructions, firmware, programming instructions or programming code (enabling, for example, the artificial pancreas application (AP App) 329 as well as the process examples of FIGS. 1 and 2) stored in memory 323, or any combination thereof. For example, the controller 321 may execute a control algorithm, such as the artificial pancreas application 329, and other programming code that may make the controller 321 operable to cause the pump to deliver doses of the drug or therapeutic agent to a user at predetermined intervals or as needed to bring blood glucose measurement values to a target blood glucose value. In an example, the AP application (App) 329 may include programming code that is operable upon execution by the controller 321 to provide the example processes for adjusting or modifying total daily insulin settings, or the like as described with reference to FIGS. 1 and 2. The user preferences for total daily insulin settings may be programmed, for example, into an artificial pancreas application 329 by the user or by a third party (such as a health care provider, medical device manufacturer, or the like) using a wired or wireless communication link, such as 331, between the medical device 302 and a personal diabetes management device 306 or other device, such as a computing device at a healthcare provider facility. In an example, the pump or medical device 302 is communicatively coupled to the PDM processor 361 of the personal diabetes management device via the wireless communication link 331 or via a wireless communication link, such as 391 from smart device 307 or 308 from the sensor 304. The pump mechanism 324 of the medical device 302 may be operable to receive an actuation signal from the PDM processor 361, and in response to receiving a command signal or an actuation signal, expel insulin from the reservoir 325 based on the commands from an AP application, such as 369.

In an operational example, the AP application 369 executing in the personal diabetes management device 306 may be operable to control delivery of insulin to a user. For example, the AP application 369 may be operable to determine timing of an insulin dose and may output a command signal to the medical device 302 that actuates the pump mechanism 324 to deliver an insulin dose. In addition, the AP application (or AID algorithm) 369 when loaded with programmed code that provides instructions for the functionality of FIGS. 1 and 2.

The other devices in the system 300, such as personal diabetes management device 306, smart device 307 and sensor 304, may also be operable to perform various functions including controlling the medical device 302. For example, the personal diabetes management device 306 may include a communication device 364, a PDM processor 361, and a personal diabetes management device memory 363. The personal diabetes management device memory 363 may store an instance of the AP application 369 that includes programming code, that when executed by the PDM processor 361 provides the process examples described with reference to the examples of FIGS. 1 and 2. The personal diabetes management device memory 363 may also store programming code for providing the process examples described with reference to the examples of FIGS. 1 and 2.

The smart device 307 may be, for example, a smart phone, an Apple Watch®, another wearable smart device, including eyeglasses, provided by other manufacturers, a global positioning system-enabled wearable, a wearable fitness device, smart clothing, or the like. Similar to the personal diabetes management device 306, the smart device 307 may also be operable to perform various functions including controlling the medical device 302. For example, the smart device 307 may include a communication device 374, a processor 371, and a memory 373. The memory 373 may store an instance of the AP application 379 and/or an instance of an AID application (not shown) that includes programming code for providing the process examples described with reference to the examples of FIGS. 2 and 3. The memory 373 may also as store programming code and be operable to store data related to the AP application 379 or an instance of an AID application (not shown). In an operational example, the AP application 379 may be operable to provide functionality similar to or the same the functionality as described with reference to the instance of the AP application 369.

The sensor 304 of system 300 may be a continuous glucose monitor (CGM) as described above, that may include a processor 341, a memory 343, a sensing or measuring device 344, and a communication device 346. The memory 343 may, for example, store an instance of an AP application 349 as well as other programming code and be operable to store data related to the AP application 349 and process examples described with reference to FIGS. 1 and 2. The AP application 349 may also include programming code for providing the process examples described with reference to the examples of FIGS. 1 and 2.

Instructions for determining the delivery of the drug or therapeutic agent (e.g., as a bolus dosage) to the user (e.g., the size and/or timing of any doses of the drug or therapeutic agent) may originate locally by the medical device 302 or may originate remotely and be provided to the medical device 302. In an example of a local determination of drug or therapeutic agent delivery, programming instructions, such as an instance of the artificial pancreas application 329, stored in the memory 323 that is coupled to the medical device 302 may be used to make determinations by the medical device 302. In addition, the medical device 302 may be operable to communicate with the cloud-based services 311 via the communication device 326 and the communication link 388. In an example, the system 300 may include one or more components operable to implement the process examples of FIGS. 1, 2, 4 and 5.

Alternatively, the remote instructions may be provided to the medical device 302 over a wired or wireless communication link (such as 331) by the personal diabetes management device (PDM) 306, which has a PDM processor 361 that executes an instance of the artificial pancreas application 369, or the smart device 307 (via communication link 391), which has a processor 371 that executes an instance of the artificial pancreas application 369 as well as other programming code for controlling various devices, such as the medical device 302, smart device 307 and/or sensor 304. In an example, the send a message to a server, for example, in the cloud services 311 or the like, requesting downloading of the one or more cost functions to a personal diabetes management (PDM) 306 or smart device 307. The medical device 302 may execute any received instructions (originating internally or from the personal diabetes management device 306) for the delivery of the drug or therapeutic agent to the user. In this way, the delivery of the drug or therapeutic agent to a user may be automatic.

In various examples, the medical device 302 may communicate via a wireless communication link 331 with the personal diabetes management device 306. The personal diabetes management device 306 may be an electronic device such as, for example, a smart phone, a tablet, a dedicated diabetes therapy personal diabetes management device, or the like. The personal diabetes management device 306 may be a wearable wireless accessory device. The wireless communication links 308, 331, 322, 391, 392 and 393 may be any type of wireless communication link provided by any known wireless standard. As an example, the wireless communication links 308, 331, 322, 391, 392 and 393 may enable communications between the medical device 302, the personal diabetes management device 306 and sensor 304 based on, for example, Bluetooth®, Wi-Fi®, a near-field communication standard, a cellular standard, or any other wireless optical or radio-frequency protocol.

The sensor 304 may be a glucose sensor operable to measure blood glucose and output a blood glucose value or data that is representative of a blood glucose value. For example, the sensor 304 may be a glucose monitor or a continuous glucose monitor (CGM). The sensor 304 may include a processor 341, a memory 343, a sensing/measuring device 344, and communication device 346. The communication device 346 of sensor 304 may include one or more sensing elements, an electronic transmitter, receiver, and/or transceiver for communicating with the personal diabetes management device 306 over a wireless communication link 322 or with medical device 302 over the link 308. The sensing/measuring device 344 may include one or more sensing elements, such as a glucose measurement, heart rate monitor, or the like. The processor 341 may include discrete, specialized logic and/or components, an application-specific integrated circuit, a microcontroller or processor that executes software instructions, firmware, programming instructions stored in memory (such as memory 343), or any combination thereof. For example, the memory 343 may store an instance of an AP application 349 that is executable by the processor 341.

Although the sensor 304 is depicted as separate from the medical device 302, in various examples, the sensor 304 and medical device 302 may be incorporated into the same unit. That is, in various examples, the sensor 304 may be a part of the medical device 302 and contained within the same housing of the medical device 302 (e.g., the sensor 304 may be positioned within or embedded within the medical device 302). Glucose monitoring data (e.g., measured blood glucose values) determined by the sensor 304 may be provided to the medical device 302, smart device 307 and/or the personal diabetes management device 306 and may be used to perform the functions and deliver doses of insulin for automatic delivery of insulin by the medical device 302 as described with reference to the examples of FIGS. 1 and 2.

The sensor 304 may also be coupled to the user by, for example, adhesive or the like and may provide information or data on one or more medical conditions and/or physical attributes of the user. The information or data provided by the sensor 304 may be used to adjust drug delivery operations of the medical device 302.

In an example, the personal diabetes management device 306 may be a mobile computing device operable to manage a personal diabetes treatment plan via an AP application or an AID algorithm. The personal diabetes management device 306 may be used to program or adjust operation of the medical device 302 and/or the sensor 304. The personal diabetes management device 306 may be any portable electronic, computing device including, for example, a dedicated controller, such as PDM processor 361, a smartphone, or a tablet. In an example, the personal diabetes management device (PDM) 306 may include a PDM processor 361, a personal diabetes management device memory 363, and a communication device 364. The personal diabetes management device 306 may contain analog and/or digital circuitry that may be implemented as a PDM processor 361 (or controller) for executing processes to manage a user's blood glucose levels and for controlling the delivery of the drug or therapeutic agent to the user. The PDM processor 361 may also be operable to execute programming code stored in the personal diabetes management device memory 363. For example, the personal diabetes management device memory 363 may be operable to store an artificial pancreas (AP) application 369 that may be executed by the PDM processor 361. The PDM processor 361 may when executing the artificial pancreas application 369 may be operable to perform various functions, such as those described with respect to the examples in FIGS. 1 and 2. The wireless communication device 364 may be a device, such as a receiver, a transmitter, or a transceiver that operates according to one or more radio-frequency protocols. For example, the communication device 364 may include a cellular transceiver and a Bluetooth transceiver that enables the personal diabetes management device 306 to communicate with a data network (not shown) via the cellular transceiver and with the sensor 304 and the medical device 302. The respective transceivers of communication device 364 may be operable to transmit signals containing information useable by or generated by the AP application or the like. The communication devices 326, 346 and 376 of respective medical device 302, sensor 304 and Smart device 307 may also be operable to transmit signals containing information useable by or generated by the AP application or the like.

The medical device 302 may communicate with the sensor 304 over a wireless communication link 308 and may communicate with the personal diabetes management device 306 over a wireless communication link 331. The sensor 304 and the personal diabetes management device 306 may communicate over a wireless communication link 322. The smart device 307, when present, may communicate with the medical device 302, the sensor 304 and the personal diabetes management device 306 over wireless communication links 391, 392 and 393, respectively. The wireless communication links 308, 331, 322, 391, 392 and 393 may be any type of wireless communication link operating using known wireless standards or proprietary standards. As an example, the wireless communication links 308, 331, 322, 391, 392 and 393 may provide communication links based on Bluetooth®, Wi-Fi, a near-field communication standard, a cellular standard, or any other wireless protocol via the respective communication devices 326, 346 and 364. In some examples, the medical device 302 and/or the personal diabetes management device 306 may include a user interface 327, 378 and 368, respectively, such as a keypad, a touchscreen display, levers, buttons, a microphone, a speaker, a light, a display, or the like, that is operable to allow a user to enter information and allow the personal diabetes management device to output information for presentation to the user. Note that the respective user interface devices 327, 378 and 368 may serve with the associated hardware, such as a touchscreen display, as both an input device and an output device. For example, the user interface devices may present graphical user interfaces that guide a user, for example, through the presentation of prompts, to input information or provide data to the user as well as other functions.

In various examples, the drug delivery system 300 may implement the artificial pancreas (AP) algorithm (and/or provide AP functionality) to govern or control automatic delivery of insulin to a user (e.g., to maintain euglycemia—a normal level of glucose in the blood). The AP application (or an AID algorithm) may be implemented by the medical device 302 and/or the sensor 304. The AP application may be operable to determine an initial total daily insulin dosage as described with reference to the examples of FIGS. 1, 2, 4 and 5, as well as the times and incremental dosages of insulin delivery. In various examples, the AP application (or the AID algorithm) may determine the times and dosages for delivery based on information known about the user, such as the user's sex, age, weight, or height, and/or on information gathered about a physical attribute or condition of the user (e.g., from the sensor 304). For example, the AP application may determine an appropriate delivery of insulin based on glucose level monitoring of the user through the sensor 304. The AP application may also allow the user to adjust insulin delivery. For example, the AP application may allow the user to issue (e.g., via an input) commands to the medical device 302, such as a command to deliver an insulin bolus. In some examples, different functions of the AP application may be distributed among two or more of the personal diabetes management device 306, the medical device 302 or the sensor 304. In other examples, the different functions of the AP application may be performed by one device, such the personal diabetes management device 306, the medical device 302 or the sensor 304.

As described herein, the drug delivery system 300 or any component thereof, such as the medical device may be considered to provide AP functionality or to implement an AP application. Accordingly, references to the AP application (e.g., functionality, operations, or capabilities thereof) are made for convenience and may refer to and/or include operations and/or functionalities of the drug delivery system 300 or any constituent component thereof (e.g., the medical device 302 and/or the personal diabetes management device 306). The drug delivery system 300—for example, as an insulin delivery system implementing an AP application—may be considered to be a drug delivery system or an AP application-based delivery system that uses sensor inputs (e.g., data collected by the sensor 304).

In an example, one or more of the devices, 302, 304, 306 or 307 may be operable to communicate via a wireless communication link 388 with cloud-based services 311. The cloud-based services 311 may utilize servers and data storage (not shown). The communication link 388 may be a cellular link, a Wi-Fi link, a Bluetooth link, or a combination thereof, that is established between the respective devices 302, 304, 306 or 307 of system 300. The data storage provided by the cloud-based services 311 may store insulin delivery history related to the user, cost function data related to general delivery of insulin to users, or the like. In addition, the cloud-based services 311 may process anonymized data from multiple users to provide generalized information related to the various parameters used by the AP application.

In an example, the device 302 includes a communication device 364, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 311. For example, outputs from the sensor 304 or the medical device 302 may be transmitted to the cloud-based services 311 for storage or processing via the transceivers of communication device 364. Similarly, medical device 302, personal diabetes management device 306 and sensor 304 may be operable to communicate with the cloud-based services 311 via the communication link 388.

In an example, the respective receiver or transceiver of each respective device, 302, 306 or 307, may be operable to receive signals containing respective blood glucose measurement values of the number of blood glucose measurement values that may be transmitted by the sensor 304. The respective processor of each respective device 302, 306 or 307 may be operable to store each of the respective blood glucose measurement values in a respective memory, such as 323, 363 or 373. The respective blood glucose measurement values may be stored as data related to the artificial pancreas algorithm, such as 329, 349, 369 or 379. In a further example, the AP application operating on any of the personal diabetes management device 306, the Smart device 307, or sensor 304 may be operable to transmit, via a transceiver implemented by a respective communication device, 364, 374, 346, a control signal for receipt by a medical device. In the example, the control signal may indicate an amount of insulin to be expelled by the medical device 302.

Various operational scenarios and examples of processes performed by the system 300 are described herein. For example, the system 300 may be operable to implement the process examples of FIGS. 1 and 2.

The techniques described herein for providing functionality to set an adjusted total daily insulin factor and determine whether the adjusted total daily insulin factor exceeds a maximum algorithm delivery threshold. In response to a result of the determination, set a total daily insulin dosage using the attained information and obtain blood glucose measurement values over a period of time. Based on the obtained blood glucose measurement values, a level of glycated hemoglobin of a user may be determined. The set total daily insulin dosage may be modified to provide a modified total daily insulin dosage in response to the determined level of glycated hemoglobin. A control signal including the modified total daily insulin dosage may be output instructing a controller to actuate delivery of insulin according to the modified total daily insulin dosage.

For example, the system 300 or any component thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Some examples of the disclosed device may be implemented, for example, using a storage medium, a computer-readable medium, or an article of manufacture which may store an instruction or a set of instructions that, if executed by a machine (i.e., processor or microcontroller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A non-transitory computer readable medium embodied with programming code executable by a processor, and the processor when executing the programming code is operable to perform functions, including functions to:
   receive a request via a graphical user interface to establish initial settings for an automatic insulin delivery device;
   receive an input of at least one physical characteristic of a user;
   determine an adjusted total daily insulin factor usable to calculate a total daily insulin dosage, wherein the adjusted total daily insulin factor is a total daily insulin per unit of a user's weight reduced by a reduction factor;

generate a comparison result by comparing the adjusted total daily insulin factor to a maximum algorithm delivery threshold;

based on the comparison result, set a total daily insulin dosage;

obtain blood glucose measurement values over a period of time;

based on the obtained blood glucose measurement values, determine a level of glycated hemoglobin of a user;

in response to the determined level of glycated hemoglobin, modify the set total daily insulin dosage to provide a modified total daily insulin dosage; and output a control signal including the modified total daily insulin dosage instructing a controller of a drug delivery device to actuate delivery of insulin according to the modified total daily insulin dosage.

2. The non-transitory computer readable medium of claim 1, further embodied with programming code executable by the processor, and the processor when executing the programming code to set the total daily insulin dosage is further operable to perform functions, including functions to:

determine that the comparison result indicates that the adjusted total daily insulin factor exceeds the maximum algorithm delivery threshold;

replace the adjusted total daily insulin factor with a predetermined total daily insulin factor; and calculate the set total daily insulin dosage using the predetermined total daily insulin factor and the weight of the user.

3. The non-transitory computer readable medium of claim 1, further embodied with programming code executable by the processor, and the processor when executing the programming code to set the total daily insulin dosage is further operable to perform functions, including functions to:

determine that the comparison result indicates that the adjusted total daily insulin factor is less than the maximum algorithm delivery threshold; and calculate the set total daily insulin dosage using the adjusted total daily insulin factor and the weight of the user.

4. The non-transitory computer readable medium of claim 1, further embodied with programming code executable by the processor, and the processor when executing the programming code is further operable to perform functions, including functions to:

generate a pairing request directed to the controller of the drug delivery device; and based on a response to the pairing request, establish a communication link with the controller, wherein the control signal is sent via the established communication link.

5. The non-transitory computer readable medium of claim 1, further embodied with programming code executable by the processor, and the processor when executing the programming code is further operable to perform functions, including functions to:

in response to receipt of the request to establish initial settings for an automatic insulin delivery device, determine an availability of an insulin delivery history for the user; and in response to the insulin delivery history for the user being unavailable, generate a prompt for the user to establish an initial setting for a total daily insulin dosage by inputting a weight of the user.

6. The non-transitory computer readable medium of claim 1, further embodied with programming code executable by the processor, and the processor when executing the programming code is further operable to perform functions, including functions to:

output a control signal instructing a controller of a drug delivery device to actuate a pump mechanism to administer insulin according to the set total daily insulin dosage.

7. The non-transitory computer readable medium of claim 1, further embodied with programming code executable by the processor, and the processor when executing the programming code is further operable to perform functions, including functions to:

identify a reduction proportion of the adjusted total daily insulin factor, wherein the adjusted total daily insulin factor includes an insulin coefficient.

8. The non-transitory computer readable medium of claim 1, further embodied with programming code executable by the processor, and the processor, when determining an adjusted total daily insulin factor usable to calculate a total daily insulin dosage, executes the programming code to be further operable to perform functions, including functions to:

evaluate the blood glucose measurement values with respect to one or more cost functions;

based on the evaluation, determine a reduction proportion to be applied to the total daily insulin per unit of the user's weight; and apply the reduction proportion to the adjusted total daily insulin factor, wherein the reduction proportion reduces the set total daily insulin dosage.

9. The non-transitory computer readable medium of claim 8, further embodied with programming code executable by the processor, and the processor executes the programming code to be further operable to perform functions, including functions to:

send a message, to a server, requesting downloading of the one or more cost functions to a personal diabetes management device.

10. The non-transitory computer readable medium of claim 1, further embodied with programming code executable by the processor, and the processor, when determining an adjusted total daily insulin factor usable to calculate a total daily insulin dosage, executes the programming code to be further operable to perform functions, including functions to:

send a request to a server, wherein the request includes either an age of a user, a weight of the user, or both for input into one or more cost functions;

receive a reduction proportion to be applied to the total daily insulin per unit of the user's weight, wherein the reduction proportion is based on the requested evaluation; and apply the reduction proportion to the adjusted total daily insulin factor, wherein the reduction proportion reduces the calculated set total daily insulin.

11. A device, comprising:

a processor operable to execute programming code and applications;

a memory coupled to the processor and operable to store programming code, an artificial pancreas application and data;

a wireless communication device operable to wirelessly communicate with a paired device and communicatively coupled to the processor;

wherein the artificial pancreas application is executable by the processor, wherein the processor, when executing the artificial pancreas application, is operable to perform functions, including functions to:
attain information associated with a user;
establish an adjusted total daily insulin factor;
determine whether the adjusted total daily insulin factor exceeds a maximum algorithm delivery threshold;
in response to a result of the determination, set a total daily insulin dosage using the attained information;
obtain blood glucose measurement values over a period of time;
based on the obtained blood glucose measurement values, determine a level of glycated hemoglobin of the user;
in response to the determined level of glycated hemoglobin, modify the set total daily insulin dosage to provide a modified total daily insulin dosage; and
output a control signal including the modified total daily insulin dosage instructing a controller to actuate delivery of insulin according to the modified total daily insulin dosage.

12. The device of claim 11, wherein the processor, when executing the artificial pancreas application, is further operable to perform functions, including functions to:
determine that a comparison result indicates that the adjusted total daily insulin factor exceeds the maximum algorithm delivery threshold;
replace the adjusted total daily insulin factor with a predetermined total daily insulin factor; and
calculate the set total daily insulin dosage using the predetermined total daily insulin factor and the attained information, wherein the attained information includes a weight of the user.

13. The device of claim 11, wherein the processor, when executing the artificial pancreas application, is further operable to perform functions, including functions to:
determine that a comparison result indicates that the adjusted total daily insulin factor is less than the maximum algorithm delivery threshold; and
calculate the set total daily insulin dosage using the adjusted total daily insulin factor and the attained information, wherein the attained information includes a weight of the user.

14. The device of claim 11, wherein:
the wireless communication device is operable to communicatively couple to a continuous blood glucose sensor,
the processor operable to receive blood glucose measurement values via the wireless communication device from the continuous blood glucose sensor, and
the processor, when executing the artificial pancreas application, is further operable to perform functions, including functions to:
generate a pairing request directed to a controller of a drug delivery device; and
based on a response to the pairing request, establish a communication link with the controller, wherein the control signal is sent via the established communication link.

15. The device of claim 11, wherein the processor, when executing the artificial pancreas application, is further operable to perform functions, including functions to:
in response to receipt of the request to establish initial settings for an automatic insulin delivery device, determine an availability of an insulin delivery history for the user; and
in response to the insulin delivery history for the user being unavailable, generate a prompt for the user to establish an initial setting for a total daily insulin dosage by inputting a weight of the user.

16. The device of claim 11, wherein the processor, when executing the artificial pancreas application, is further operable to perform functions, including functions to:
output a control signal instructing a controller of a drug delivery device to actuate a pump mechanism to administer insulin according to the set total daily insulin dosage.

17. The device of claim 11, wherein the processor, when executing the artificial pancreas application, is further operable to perform functions, including functions to:
store the attained information in the memory as data, wherein the attained information includes a weight of a user, an age of a user, or both.

18. The device of claim 11, wherein the processor, when executing the artificial pancreas application, is further operable to perform functions, including functions to:
evaluate the blood glucose measurement values with respect to one or more cost functions;
based on the evaluation, determine a reduction proportion to be applied to a total daily insulin per unit of a user's weight, wherein the attained information includes the user's weight; and
apply the reduction proportion to the adjusted total daily insulin factor, wherein the reduction proportion reduces the calculated set total daily insulin.

19. The device of claim 18, wherein the processor, when executing the artificial pancreas application, is further operable to perform functions, including functions to:
send a request, to a server, requesting the one or more cost functions; and
in response to the request, receive the one or more cost function from the server.

20. The device of claim 11, wherein the processor, when executing the artificial pancreas application, is further operable to perform functions, including functions to:
send a request to a server, wherein the request includes either an age of a user, a weight of the user, or both for input into one or more cost functions;
receive a reduction proportion to be applied to a total daily insulin per unit of a user's weight, wherein the reduction proportion is based on a result of an evaluation performed in response to the request; and
apply the reduction proportion to the adjusted total daily insulin factor, wherein the reduction proportion reduces the set total daily insulin dosage.

* * * * *